(12) United States Patent
Richman et al.

(10) Patent No.: US 8,092,816 B2
(45) Date of Patent: Jan. 10, 2012

(54) INSECTICIDAL COMPOSITIONS FOR CONTROL OF GENERAL HOUSEHOLD PESTS

(75) Inventors: Dina L. Richman, Philadelphia, PA (US); James B. Ballard, Medford, NJ (US); Kim Watson, Cherry Hill, NJ (US); Cristi L. Palmer, Hightstown, NJ (US)

(73) Assignee: FMC Corporation, Philadelphia, PA (US)

( * ) Notice: Subject to any disclaimer, the term of this patent is extended or adjusted under 35 U.S.C. 154(b) by 632 days.

(21) Appl. No.: 10/585,426

(22) PCT Filed: Jan. 7, 2005

(86) PCT No.: PCT/US2005/000584
§ 371 (c)(1),
(2), (4) Date: Aug. 5, 2008

(87) PCT Pub. No.: WO2005/070210
PCT Pub. Date: Aug. 4, 2005

(65) Prior Publication Data
US 2008/0319023 A1    Dec. 25, 2008

Related U.S. Application Data

(60) Provisional application No. 60/535,667, filed on Jan. 9, 2004.

(51) Int. Cl.
*A01N 25/02* (2006.01)
*A01N 43/40* (2006.01)
(52) U.S. Cl. ......... 424/405; 424/406; 514/341; 514/531
(58) Field of Classification Search .................. None
See application file for complete search history.

(56) References Cited

U.S. PATENT DOCUMENTS

| | | | |
|---|---|---|---|
| 5,661,164 | A | 8/1997 | Otsu et al. |
| 6,284,782 | B1 | 9/2001 | Fujimoto |
| 6,555,092 | B2 | 4/2003 | Sembo |
| 2004/0053786 | A1 | 3/2004 | Selby |
| 2004/0161441 | A1 | 8/2004 | Sirinyan |

FOREIGN PATENT DOCUMENTS

| | | |
|---|---|---|
| CN | 1 234 181 A | 11/1999 |
| DE | 101 17 676 A1 | 10/2002 |
| EP | 0 387 663 A1 | 9/1990 |
| FR | 2 784 011 A1 | 4/2000 |
| JP | 63-126805 A | 5/1988 |
| WO | WO 02/28186 A2 | 4/2002 |
| WO | WO 02/30200 A1 | 4/2002 |
| WO | WO 02/43494 A2 | 6/2002 |
| WO | WO 02/078443 A1 | 10/2002 |
| WO | WO 02/087338 A1 | 11/2002 |
| WO | WO 2004/064517 A2 | 8/2004 |
| WO | WO 2004/064522 A1 | 8/2004 |
| WO | WO 2004/098290 A1 | 11/2004 |
| WO | WO 2005/015993 A1 | 2/2005 |

OTHER PUBLICATIONS

Soika, Grazyna "Effectiveness of Some Insecticides in the Control of Macrosteles Laevis (Rib) and Protection of Annual Ornamental Plants Against Aster Yellow (AY) Phytoplasma," Journal of Fruit and Ornamental Plant Research, 2000, pp. 155 to 167, vol. VIII No. 3-4, Skierniewice, Poland.
Greene, et al. "Management of Stink Bugs Using Symptoms of Boll Injury as a Monitoring Tool", Proc. Beltwide Cotton Conf., Univ. of Georgia, (1993, vol. 2, pp. 1041-1044). CROPU 2009 Thomson Reuters on STN, Abstract.
Cao, Mingzhang, et al. Modern Pesticide No. 3 (2002), pp. 13-15.

*Primary Examiner* — Neil Levy

(57) ABSTRACT

The present invention relates to an insecticidal composition comprising a pyrethroid and a second insecticide selected from the group consisting of imidacloprid, nithiazine, thiamethoxam, dinotefuran, nitenpyram, thiacloprid, clothianidin and chlorfenapyr, with significantly improved knockdown and mortality characteristics when applied to general household pests.

8 Claims, No Drawings

INSECTICIDAL COMPOSITIONS FOR CONTROL OF GENERAL HOUSEHOLD PESTS

This application claims the benefit of U.S. Provisional Application No. 60/535,667, filed Jan. 9, 2004.

FIELD OF THE INVENTION

The present invention relates generally to insecticidal compositions. In particular, it pertains to compositions of insecticides useful for control of general household pests.

BACKGROUND OF THE INVENTION

General household pests are insects that have the potential to cause nuisance or harm to person and property, such as the German cockroach, American cockroach, Smokey-Brown cockroach, Oriental cockroach, house fly, biting fly, filth fly, red imported fire ant (RIFA), odorous house ant, carpenter ant, pharaoh ant, Argentine ant, mosquito, tick, flea, sowbug, pillbug, centipede, spider, silverfish, scorpion and bed bug. The following are some examples of nuisance or harm to persons and property. Cockroaches and flies can appear in people's living environment at any place and at any time. They generally contaminate food and articles subjecting people to threats of bacteria and viruses. The continued proliferation of colonies of red imported fire ants, *Solenopsis invicta*, are becoming a serious problem in the United States. Fire ants are attracted to electrical circuits and can cause failures in transformers, cables, connectors and related electrical hardware. Fire ants also can sting persons or animals and generally cause a localized allergic reaction on the area of the skin punctured by their stinging. Some individuals suffer a severe allergic reaction that can lead to anaphylactic shock, which can be fatal if not treated promptly. Many of the general household pests are potentially dangerous since their bites or stings can similarly lead to allergic reaction.

Insecticidal compositions have commonly been used to control general household pests. Of primary concern in developing an insecticidal composition to control general household pests is the insecticide's 'knockdown' and 'mortality' characteristics. Knockdown refers to quick, short-term immobilization or death of the pest. Pests can recover from knockdown immobilization. Knockdown usually occurs within 10-30 minutes, but the timing is pest dependant. For example, knockdown for house flies can occur at up to 2 hours because of their tolerance for insecticides and recovery abilities. Mortality refers to death of the pest. An optimal insecticide composition would have knockdown and mortality rates at or near 100% for all general household pests. Current insecticidal compositions, for example, have red imported fire ant and German cockroach mortality rates approaching 100%, but their knockdown rates are only 80% or less for red imported fire ants and 40% or less for German cockroaches. Improved knockdown rates and for many pests improved mortality rates are desirable to ensure effective protection of persons and property from general household pests.

SUMMARY OF THE INVENTION

It has now been unexpectedly found that applications of an insecticidal composition containing a mixture of a pyrethroid and a second insecticide selected from the group consisting of imidacloprid, nithiazine, thiamethoxam, dinotefuran, nitenpyram, thiacloprid, clothianidin and chlorfenapyr, results in a continuous chemical barrier that provides both high knockdown and mortality rates when applied to general household pests. Other aspects of the present invention will also be apparent.

DETAILED DESCRIPTION OF THE INVENTION

It has now been unexpectedly found that an insecticidal composition containing a mixture of a pyrethroid and a second insecticide selected from the group consisting of imidacloprid, nithiazine, thiamethoxam, dinotefuran, nitenpyram, thiacloprid, clothianidin and chlorfenapyr, results in high knockdown and mortality rates when applied to general household pests. Preferred compositions are those wherein the pyrethroid is bifenthrin, cypermethrin, zeta cypermethrin, lambdacyhalothrin, betacyhalothrin, alphacypermethrin, tralomethrin, deltamethrin, cyfluthrin, beta-cyfluthrin, esfenvalerate, fluvalinate, etofenprox, permethrin, metofluthrin, resmethrin, bioresmethrin, allethrin, bioallethrin, s-bioallethrin or tetramethrin. Further preferred compositions are those wherein the pyrethroid is bifenthrin.

A preferred embodiment of the present invention is a composition wherein the second insecticide is selected from the group consisting of imidacloprid, thiamethoxam and clothianidin. More preferred compositions of the present invention are comprised of from 0.001% by weight to 0.20% by weight of the second insecticide.

Another embodiment of the present invention is a method for controlling general household pests comprising applying an insecticidally effective amount of a composition comprised of a pyrethroid and a second insecticide selected from the group consisting of imidacloprid, nithiazine, thiamethoxam, dinotefuran, nitenpyram, thiacloprid, clothianidin and chlorfenapyr to a locus where general household pest control is needed or expected to be needed. Preferred general household pests are selected from German cockroach, American cockroach, Smokey-Brown cockroach, Oriental cockroach, house fly, biting fly, filth fly, red imported fire ant (RIFA), odorous house ant, carpenter ant, pharaoh ant, Argentine ant, mosquito, tick, flea, sowbug, pillbug, centipede, spider, silverfish, scorpion and bed bug. Preferred locus or loci are selected from a general household pest-infested structure, a structure that is expected to be general household pest-infested, or a location adjacent to the structures.

The amount of each insecticide in the composition can be varied over a wide range depending upon the target pest and the level of control desired. For controlling German cockroaches, preferred liquid insecticide compositions of the present invention are comprised of from 0.001% by weight to 0.005% by weight of bifenthrin and from 0.01% by weight to 0.02% by weight of thiamethoxam; from 0.001% by weight to 0.06% by weight of bifenthrin and from 0.01% by weight to 0.10% by weight of imidicloprid; and from 0.001% by weight to 0.005% by weight of bifenthrin and from 0.01% by weight to 0.02% by weight of clothianidin. For controlling American cockroaches, preferred liquid insecticide compositions of the present invention are comprised of from 0.001% by weight to 0.005% by weight of bifenthrin and from 0.01% by weight to 0.02% by weight of thiamethoxam; from 0.001% by weight to 0.005% by weight of bifenthrin and from 0.01% by weight to 0.02% by weight of imidicloprid; and from 0.001% by weight to 0.005% by weight of bifenthrin and from 0.01% by weight to 0.02% by weight of clothianidin. For controlling Oriental cockroaches, preferred liquid insecticide compositions of the present invention are comprised of from 0.001% by weight to 0.005% by weight of bifenthrin and from 0.0175% by weight to 0.0225% by weight of thiamethoxam; from 0.001% by weight to 0.005% by weight of bifenthrin and from 0.01% by weight to 0.02% by weight of imidicloprid; and from 0.001% by weight to 0.005% by weight of bifenthrin and from 0.01% by weight to 0.02% by weight of clothianidin. For controlling red imported fire ants (RIFA), preferred liquid insecticide compositions of the present invention are comprised of from 0.001% by weight to 0.06% by weight of bifenthrin and from 0.01% by weight to 0.10% by weight of imidicloprid; and from 0.001% by weight to 0.005% by weight of bifenthrin and from 0.01% by weight to 0.02% by weight of clothianidin. For controlling house flies, preferred liquid insecticide compositions of the present invention are comprised of from 0.001% by weight to 0.005% by weight of bifenthrin and from 0.0025% by weight to 0.02% by weight of thiamethoxam; from 0.001% by weight to 0.005% by weight of bifenthrin and from 0.01% by weight to 0.02% by weight of imidicloprid; and from 0.001% by weight to 0.005% by weight of bifenthrin and from 0.01% by weight to 0.02% by weight of clothianidin. For controlling Yellow Fever Mosquitoes, a preferred liquid insecticide composition of the present invention is comprised of 0.001% by weight to 0.005% by weight of bifenthrin and 0.01% by weight to 0.02% by weight of clothianidin.

A liquid insecticide is any formulation containing an insecticide where the formulation is dispensed in an aqueous medium prior to its application to a locus where general household pest control is needed. That is to say, a liquid insecticide is made up of 1) an insecticide, 2) an aqueous medium and 3) other additives conventionally employed in insecticidal formulations (e.g. surfactants, wetting agents, freeze/thaw agents). All formulations of insecticides that are or can be dispensed in an aqueous medium prior to application are, therefore, within the scope of the present invention (e.g. Micro-emulsions, Suspension concentrates, Emulsifiable concentrates, Wettable powders, Water dispersible granules, Capsule suspensions, Emulsifiable granules or combinations thereof).

The compositions of the present invention may be prepared from commercially available formulations of insecticides. For example, bifenthrin, sold by FMC Corporation under the names and trademarks of TALSTAR® GC FLOWABLE INSECTICIDE/MITICIDE, or TALSTARONE® MULTI-INSECTICIDE, to name a few, find utility in the present invention. A formulation of imidicloprid that is particularly useful in the context of the present invention includes, without limitation, imidicloprid (sold under the name and trademark of MERIT), sold as a wettable powder (WP). A formulation of thiamethoxam that is particularly useful in the context of the present invention includes, without limitation, thiamethoxam (sold under the name and trademark of CENTRIC), sold as a 25% water dispersible granular (WDG). A formulation of clothianidin that is particularly useful in the context of the present invention includes, without limitation, clothianidin as a 16% water dispersible granular (WDG). Using methods known to one skilled in the art, the above-mentioned formulations of insecticides can be dispersed in an aqueous medium to provide a composition containing an insecticidally effective amount of an insecticide.

The following examples further illustrate the present invention, but, of course, should not be construed as in any way limiting its scope. The examples set forth certain biological data illustrating the efficacy of the compositions of the present invention in controlling general household pests. Each example embodies a separate test wherein the pests were randomly selected from a population at a random age. As a result, from example to example, the ages of the pests can be very different. This age difference potentially translates to different baselines for each example. Therefore, data should only be compared within the example and not from example to example due to the differences in age of the pests from example to example. Unless otherwise indicated, all parts, percentages, and the like are by weight. The spray chamber used in the examples was approximately 76 inches tall, 73 inches long and 31 inches deep with an adjustable shelf (approximately 22 inches deep) and a movable spray nozzle. The spray chambers were calibrated to deliver a volume of approximately 1 gallon of liquid per 1000 square feet of area at about 14 pounds per square inch of pressure. A DeVilbiss hand held sprayer (Atomizer model 152) manufactured by DeVilbiss located in Glendale Heights, Ill. was used in testing house flies and mosquitoes. The DeVilbiss was used to apply approximately 3-5 milliliters of product at about 10 pounds per square inch.

EXAMPLE 1

Test to Determine German Cockroach Mortality Rates by Applications of Combinations of Bifenthrin and Imidacloprid The compositions of the present invention were tested for German cockroach activity in the following manner:

Test compositions made up of TALSTARONE® MULTI-INSECTICIDE and a wettable powder of imidacloprid (MERIT) in distilled water were prepared that provided appropriate rates of application of combinations of bifenthrin and imidacloprid, as well as bifenthrin and imidacloprid alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male German cockroaches were placed inside each PVC ring. The sprayer was activated and the test compound was applied to each PVC ring interior. German cockroach mortality was measured. The following results were recorded:

TABLE 1

Mortality of German Cockroach by Application of Combinations of Bifenthrin and Imidacloprid

| Treatment | Rate of Appln. (PPM) | Rate of Appln. (% by weight) | Mortality Rate @ 60 minutes (%) | Mortality Rate @ 120 minutes (%) | Mortality Rate @ 1 day (%) | Mortality Rate @ 2 days (%) |
|---|---|---|---|---|---|---|
| A | 10 | 0.001 | 3 | 33 | 33 | 60 |
|   | 50 | 0.005 | 30 | 48 | 58 | 100 |

TABLE 1-continued

Mortality of German Cockroach by Application of Combinations of Bifenthrin and Imidacloprid

| Treatment | Rate of Appln. (PPM) | Rate of Appln. (% by weight) | Mortality Rate @ 60 minutes (%) | Mortality Rate @ 120 minutes (%) | Mortality Rate @ 1 day (%) | Mortality Rate @ 2 days (%) |
|---|---|---|---|---|---|---|
| B | 100 | 0.01 | 15 | 18 | 20 | 20 |
|   | 200 | 0.02 | 15 | 18 | 18 | 23 |
| A + B | 10/100 | 0.001/0.01 | 50 | 60 | 68 | 85 |
| A + B | 10/200 | 0.001/0.02 | 63 | 73 | 73 | 100 |
|   | 50/100 | 0.005/0.01 | 100 | 100 | 100 | 100 |
|   | 50/200 | 0.005/0.02 | 100 | 100 | 100 | 100 |
| Untreated | 0 | 0 | 0 | 0 | 0 | 3 |

A is bifenthrin
B is imidacloprid

EXAMPLE 2

Test to Determine German Cockroach Knockdown and Mortality Rates by Applications of Combinations of Bifenthrin and Imidacloprid The compositions of the present invention were tested for German cockroach activity in the following manner:

Test compositions made up of TALSTARONE® MULTI-INSECTICIDE and a wettable powder of imidacloprid (MERIT) in distilled water were prepared that provided appropriate rates of application of combinations of bifenthrin and imidacloprid, as well as bifenthrin and imidacloprid alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male German cockroaches were placed inside each PVC ring. The sprayer was activated and the test compound was applied to each PVC ring interior. German cockroach knockdown and mortality were measured. The following results were recorded:

TABLE 2

Knockdown and Mortality of German Cockroach by Application of Combinations of Bifenthrin and Imidacloprid

| Treatment | Rate of Appln. (PPM) | Rate of Appln. (% by weight) | Knockdown Rate @ 10 minute (%) | Knockdown Rate @ 15 minute (%) | Knockdown Rate @ 30 minutes (%) | Mortality Rate @ 60 minutes (%) | Mortality Rate @ 120 minutes (%) | Mortality Rate @ 1 day (%) |
|---|---|---|---|---|---|---|---|---|
| A | 200 | 0.02 | 0 | 3 | 45 | 100 | 100 | 100 |
|   | 600 | 0.06 | 0 | 8 | 60 | 100 | 100 | 100 |
| B | 250 | 0.025 | 5 | 20 | 50 | 75 | 75 | 70 |
|   | 500 | 0.05 | 3 | 20 | 83 | 95 | 100 | 83 |
|   | 1000 | 0.10 | 10 | 23 | 73 | 100 | 100 | 90 |
| A + B | 200/250 | 0.02/0.025 | 0 | 10 | 68 | 98 | 100 | 100 |
|   | 200/500 | 0.02/0.05 | 15 | 50 | 98 | 100 | 100 | 100 |
|   | 200/1000 | 0.02/0.10 | 28 | 75 | 93 | 100 | 100 | 100 |
|   | 600/250 | 0.06/0.025 | 15 | 60 | 90 | 100 | 100 | 100 |

TABLE 2-continued

Knockdown and Mortality of German Cockroach by Application of Combinations of Bifenthrin and Imidacloprid

| Treatment | Rate of Appln. (PPM) | Rate of Appln. (% by weight) | Knockdown Rate @ 10 minute (%) | Knockdown Rate @ 15 minute (%) | Knockdown Rate @ 30 minutes (%) | Mortality Rate @ 60 minutes (%) | Mortality Rate @ 120 minutes (%) | Mortality Rate @ 1 day (%) |
|---|---|---|---|---|---|---|---|---|
| | 600/500 | 0.06/0.05 | 15 | 60 | 95 | 100 | 100 | 100 |
| | 600/1000 | 0.06/0.10 | 20 | 58 | 95 | 100 | 100 | 100 |
| Untreated | 0 | 0 | 0 | 0 | 0 | 0 | 0 | 0 |

A is bifenthrin
B is imidacloprid

EXAMPLE 3

Test to Determine American Cockroach Knockdown and Mortality Rates by Applications of Combinations of Bifenthrin and Imidacloprid The compositions of the present invention were tested for American cockroach activity in the following manner:

Test compositions made up of TALSTARONE® MULTI-INSECTICIDE and a wettable powder of imidacloprid (MERIT) in distilled water were prepared that provided appropriate rates of application of combinations of bifenthrin and imidacloprid, as well as bifenthrin and imidacloprid alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male American cockroaches were placed inside each PVC ring. The sprayer was activated and the test compound was applied to each PVC ring interior. American cockroach knockdown and mortality were measured. The following results were recorded:

EXAMPLE 4

Test to Determine Oriental Cockroach Knockdown and Mortality Rates by Applications of Combinations of Bifenthrin and Imidacloprid The compositions of the present invention were tested for Oriental cockroach activity in the following manner:

Test compositions made up of TALSTARONE® MULTI-INSECTICIDE and a wettable powder of imidacloprid (MERIT) in distilled water were prepared that provided appropriate rates of application of combinations of bifenthrin and imidacloprid, as well as bifenthrin and imidacloprid alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male Oriental cockroaches were placed inside each PVC ring. The sprayer was activated and the test compound was applied to each PVC ring interior. Oriental cockroach knockdown and mortality were measured. The following results were recorded:

TABLE 3

Knockdown and Mortality of American Cockroach by Application of Combinations of Bifenthrin and Imidacloprid

| Treatment | Rate of Appln. (PPM) | Rate of Appln. (% by weight) | Knockdown Rate @ 15 minute (%) | Knockdown Rate @ 30 minute (%) | Mortality Rate @ 60 minutes (%) | Mortality Rate @ 120 minutes (%) | Mortality Rate @ 4 hours (%) | Mortality Rate @ 1 day (%) | Mortality Rate @ 2 days (%) |
|---|---|---|---|---|---|---|---|---|---|
| A | 10 | 0.001 | 0 | 0 | 0 | 0 | 5 | 15 | 25 |
| | 50 | 0.005 | 0 | 0 | 5 | 5 | 10 | 65 | 70 |
| B | 100 | 0.01 | 0 | 5 | 0 | 5 | 25 | 60 | 65 |
| | 200 | 0.02 | 0 | 0 | 0 | 0 | 15 | 35 | 45 |
| A + B | 10/100 | 0.001/0.01 | 0 | 5 | 10 | 10 | 55 | 75 | 80 |
| | 10/200 | 0.001/0.02 | 0 | 10 | 10 | 10 | 50 | 70 | 75 |
| | 50/100 | 0.005/0.01 | 5 | 30 | 35 | 40 | 95 | 95 | 95 |
| | 50/200 | 0.005/0.02 | 5 | 15 | 15 | 25 | 65 | 80 | 100 |
| Untreated | 0 | 0 | 0 | 0 | 0 | 0 | 0 | 0 | 0 |

A is bifenthrin
B is imidacloprid

TABLE 4

Knockdown and Mortality of Oriental Cockroach by Application of Combinations of Bifenthrin and Imidacloprid

| Treatment | Rate of Appln. (PPM) | Rate of Appln. (% by weight) | Knockdown Rate @ 15 minute (%) | Knockdown Rate @ 30 minute (%) | Mortality Rate @ 60 minute (%) | Mortality Rate @ 120 minute (%) | Mortality Rate @ 4 hours (%) | Mortality Rate @ 1 day (%) | Mortality Rate @ 2 days (%) |
|---|---|---|---|---|---|---|---|---|---|
| A | 10 | 0.001 | 0 | 0 | 0 | 0 | 0 | 15 | 15 |
|   | 50 | 0.005 | 0 | 0 | 5 | 5 | 30 | 70 | 70 |
| B | 100 | 0.01 | 0 | 0 | 0 | 10 | 70 | 70 | 75 |
|   | 200 | 0.02 | 0 | 0 | 0 | 5 | 80 | 85 | 95 |
| A + B | 10/100 | 0.001/0.01 | 0 | 20 | 20 | 70 | 100 | 100 | 100 |
|   | 10/200 | 0.001/0.02 | 0 | 30 | 30 | 100 | 100 | 100 | 100 |
|   | 50/100 | 0.005/0.01 | 0 | 45 | 45 | 100 | 100 | 100 | 100 |
|   | 50/200 | 0.005/0.02 | 0 | 45 | 45 | 100 | 100 | 100 | 100 |
| Untreated | 0 | 0 | 0 | 0 | 0 | 0 | 0 | 0 | 0 |

A is bifenthrin
B is imidacloprid

EXAMPLE 5

Test to Determine Red Imported Fire Ant Knockdown and Mortality Rates by Applications of Combinations of Bifenthrin and Imidacloprid The compositions of the present invention were tested for red imported fire ant activity in the following manner:

Test compositions made up of TALSTARONE® MULTI-INSECTICIDE and a wettable powder of imidacloprid (MERIT) in distilled water were prepared that provided appropriate rates of application of combinations of bifenthrin and imidacloprid, as well as bifenthrin and imidacloprid alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. The red imported fire ants to be treated were collected and placed in screened 16 oz paper cups. The paper cups were placed onto the aluminum foil on the spray chamber shelf. The sprayer was activated and the test compound was applied to each paper cup interior. Red imported fire ant knockdown and mortality were measured. The following results were recorded:

TABLE 5

Knockdown and Mortality of Red Imported Fire Ant by Application of Combinations of Bifenthrin and Imidacloprid

| Treatment | Rate of Appln. (PPM) | Rate of Appln. (% by weight) | Knockdown Rate @ 5 minute (%) | Knockdown Rate @ 10 minute (%) | Knockdown Rate @ 15 minute (%) | Knockdown Rate @ 30 minutes (%) | Mortality Rate @ 60 minutes (%) | Mortality Rate @ 120 minutes (%) | Mortality Rate @ 4 hours (%) | Mortality Rate @ 1 day (%) |
|---|---|---|---|---|---|---|---|---|---|---|
| A | 10 | 0.001 | 30 | 93 | 95 | 100 | 65 | 100 | 100 | 100 |
|   | 50 | 0.005 | 10 | 70 | 95 | 100 | 100 | 100 | 100 | 100 |
| B | 100 | 0.01 | 15 | 25 | 55 | 93 | 78 | 95 | 100 | 100 |
|   | 200 | 0.02 | 5 | 10 | 20 | 30 | 48 | 100 | 100 | 100 |
| A + B | 10/100 | 0.001/0.01 | 35 | 95 | 100 | 100 | 100 | 100 | 100 | 100 |
|   | 10/200 | 0.001/0.02 | 15 | 70 | 98 | 100 | 100 | 100 | 100 | 100 |
|   | 50/100 | 0.005/0.01 | 50 | 80 | 100 | 100 | 100 | 100 | 100 | 100 |
|   | 50/200 | 0.005/0.02 | 35 | 95 | 98 | 100 | 100 | 100 | 100 | 100 |
| Untreated | 0 | 0 | 0 | 0 | 0 | 0 | 0 | 0 | 0 | 0 |

A is bifenthrin
B is imidacloprid

EXAMPLE 6

Test to Determine Red Imported Fire Ant Knockdown and Mortality Rates by Applications of Combinations of Bifenthrin and Imidacloprid The compositions of the present invention were tested for red imported fire ant activity in the following manner:

Test compositions made up of TALSTARONE® MULTI-INSECTICIDE and a wettable powder of imidacloprid (MERIT) in distilled water were prepared that provided appropriate rates of application of combinations of bifenthrin and imidacloprid, as well as bifenthrin and imidacloprid alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. The red imported file ants to be treated were collected and placed in screened 16 oz paper cups. The paper cups were placed onto the aluminum foil on the spray chamber shelf. The sprayer was activated and the test compound was applied to each paper cup interior. Red imported fire ant knockdown and mortality were measured. The following results were recorded:

EXAMPLE 7

Test to Determine House Fly Knockdown and Mortality Rates by Applications of Combinations of Bifenthrin and Imidacloprid The compositions of the present invention were tested for house fly activity in the following manner:

Test compositions made up of TALSTARONE® MULTI-INSECTICIDE and a wettable powder of imidacloprid (MERIT) in distilled water were prepared that provided appropriate rates of application of combinations of bifenthrin and imidacloprid, as well as bifenthrin and imidacloprid alone.

A DeVilbiss hand held sprayer was used to deliver the treatment solution at the desired volume and pressure. The house flies to be treated were collected and placed in screened 16 oz paper cups. The hand held sprayer was activated and the test compound was applied to each paper cup interior. House fly knockdown and mortality were measured. The following results were recorded:

TABLE 6

Knockdown and Mortality of Red Imported Fire Ant by Application of Combinations of Bifenthrin and Imidacloprid

| Treatment | Rate of Appln. (PPM) | Rate of Appln. (% by weight) | Knockdown Rate @ 5 minute (%) | Knockdown Rate @ 10 minute (%) | Knockdown Rate @ 15 minute (%) | Knockdown Rate @ 30 minutes (%) | Mortality Rate @ 60 minutes (%) | Mortality @ 120 minutes (%) | Mortality Rate @ 4 hours (%) |
|---|---|---|---|---|---|---|---|---|---|
| A | 200 | 0.02 | 0 | 0 | 70 | 88 | 100 | 100 | 100 |
|   | 600 | 0.06 | 0 | 40 | 88 | 100 | 100 | 100 | 100 |
| B | 250 | 0.025 | 0 | 0 | 0 | 5 | 73 | 100 | 000 |
|   | 500 | 0.05 | 0 | 0 | 0 | 10 | 88 | 100 | 100 |
|   | 1000 | 0.10 | 0 | 0 | 3 | 33 | 98 | 100 | 100 |
| A + B | 200/250 | 0.02/0.025 | 3 | 5 | 15 | 100 | 98 | 100 | 100 |
|   | 200/500 | 0.02/0.05 | 0 | 8 | 50 | 100 | 100 | 100 | 100 |
|   | 200/1000 | 0.02/0.10 | 0 | 10 | 80 | 100 | 100 | 100 | 100 |
|   | 600/250 | 0.06/0.025 | 0 | 65 | 100 | 100 | 100 | 100 | 100 |
| A + B | 600/500 | 0.06/0.05 | 15 | 83 | 100 | 100 | 100 | 100 | 100 |
|   | 600/1000 | 0.06/0.10 | 43 | 98 | 100 | 100 | 100 | 100 | 100 |
| Untreated | 0 | 0 | 0 | 0 | 0 | 0 | 0 | 0 | 0 |

A is bifenthrin

B is imidacloprid

TABLE 7

Knockdown and Mortality of House Fly by Application of Combinations of Bifenthrin and Imidacloprid

| Treatment | Rate of Appln. (PPM) | Rate of Appln. (% by weight) | Knockdown Rate @ 15 minute (%) | Knockdown Rate @ 30 minute (%) | Knockdown Rate @ 45 minutes (%) | Knockdown Rate @ 60 minutes (%) | Knockdown Rate @ 120 minutes (%) | Knockdown Rate @ 4 hours (%) | Mortality Rate @ 1 day (%) |
|---|---|---|---|---|---|---|---|---|---|
| A | 10 | 0.001 | 0 | 0 | 17 | 40 | 63 | 50 | 30 |
|   | 50 | 0.005 | 0 | 78 | 97 | 97 | 97 | 97 | 97 |
| B | 100 | 0.01 | 42 | 91 | 91 | 100 | 94 | 94 | 97 |
|   | 200 | 0.02 | 62 | 100 | 100 | 100 | 95 | 97 | 97 |
| A + B | 10/100 | 0.001/ 0.01 | 44 | 94 | 94 | 94 | 94 | 94 | 72 |
| A + B | 10/200 | 0.001/ 0.02 | 88 | 97 | 94 | 97 | 97 | 100 | 82 |
|   | 50/100 | 0.005/ 0.01 | 69 | 100 | 100 | 100 | 100 | 100 | 100 |
|   | 50/200 | 0.005/ 0.02 | 87 | 100 | 100 | 100 | 100 | 100 | 97 |
| Untreated | 0 | 0 | 0 | 0 | 0 | 0 | 0 | 0 | 0 |

A is bifenthrin
B is imidacloprid

EXAMPLE 8

Test to Determine German Cockroach Mortality Rates by Applications of Combinations of Bifenthrin and Thiamethoxam The compositions of the present invention were tested for German cockroach activity in the following manner:

Test compositions made up of TALSTARONE® MULTI-INSECTICIDE and a water dispersible granular of thiamethoxam (CENTRIC) in distilled water were prepared that provided appropriate rates of application of combinations of bifenthrin and thiamethoxam, as well as bifenthrin and thiamethoxam alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male German cockroaches were placed inside each PVC ring. The sprayer was activated and the test compound was applied to each PVC ring interior. German cockroach mortality was measured. The following results were recorded:

TABLE 8

Mortality of German Cockroach by Application of Combinations of Bifenthrin and Thiamethoxam

| Treatment | Rate of Appln. (PPM) | Rate of Appln. (% by weight) | Mortality Rate @ 60 minutes (%) | Mortality Rate @ 120 minutes (%) | Mortality Rate @ 1 day (%) | Mortality Rate @ 2 day (%) | Mortality Rate @ 4 days (%) |
|---|---|---|---|---|---|---|---|
| A | 10 | 0.001 | 8 | 33 | 35 | 60 | 98 |
|   | 50 | 0.005 | 15 | 48 | 58 | 100 | 100 |
| B | 100 | 0.01 | 0 | 45 | 90 | 93 | 93 |
|   | 200 | 0.02 | 13 | 63 | 98 | 100 | 100 |
| A + B | 10/100 | 0.001/ 0.01 | 5 | 50 | 95 | 100 | 100 |
|   | 10/200 | 0.001/ 0.02 | 38 | 75 | 100 | 100 | 100 |
|   | 50/100 | 0.005/ 0.01 | 33 | 80 | 100 | 100 | 100 |
|   | 50/200 | 0.005/ 0.02 | 40 | 88 | 100 | 100 | 100 |
| Untreated | 0 | 0 | 0 | 0 | 0 | 3 | 5 |

A is bifenthrin
B is thiamethoxam

EXAMPLE 9

Test to Determine American Cockroach Knockdown and Mortality Rates by Applications of Combinations of Bifenthrin and Thiamethoxam The compositions of the present invention were tested for American cockroach activity in the following manner:

Test compositions made up of TALSTARONE® MULTI-INSECTICIDE and a water dispersible granular of thiamethoxam (CENTRIC) in distilled water were prepared that provided appropriate rates of application of combinations of bifenthrin and thiamethoxam, as well as bifenthrin and thiamethoxam alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male American cockroaches were placed inside each PVC ring. The sprayer was activated and the test compound was applied to each PVC ring interior. American cockroach knockdown and mortality were measured. The following results were recorded:

EXAMPLE 10

Test to Determine Oriental Cockroach Knockdown and Mortality Rates by Applications of Combinations of Bifenthrin and Thiamethoxam The compositions of the present invention were tested for Oriental cockroach activity in the following manner:

Test compositions made up of TALSTARONE® MULTI-INSECTICIDE and a water dispersible granular of thiamethoxam (CENTRIC) in distilled water were prepared that provided appropriate rates of application of combinations of bifenthrin and thiamethoxam, as well as bifenthrin and thiamethoxam alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male Oriental cockroaches were placed inside each PVC ring. The sprayer was activated and the test compound was applied to each PVC ring interior. Oriental cockroach knockdown and mortality were measured. The following results were recorded:

TABLE 9

Knockdown and Mortality of American Cockroach by Application of Combinations of Bifenthrin and Thiamethoxam

| Treatment | Rate of Appln. (PPM) | Rate of Appln. (% by weight) | Knockdown Rate @ 15 minute (%) | Knockdown Rate @ 30 minute (%) | Mortality Rate @ 60 minutes (%) | Mortality Rate @ 120 minutes (%) | Mortality Rate @ 4 hours (%) | Mortality Rate @ 1 day (%) |
|---|---|---|---|---|---|---|---|---|
| A | 10 | 0.001 | 0 | 0 | 0 | 0 | 0 | 5 |
|   | 50 | 0.005 | 0 | 0 | 0 | 0 | 0 | 30 |
| B | 100 | 0.01 | 0 | 0 | 0 | 0 | 0 | 20 |
|   | 200 | 0.02 | 0 | 0 | 0 | 0 | 10 | 35 |
| A + B | 10/100 | 0.001/0.01 | 0 | 5 | 0 | 0 | 5 | 35 |
| A + B | 10/200 | 0.001/0.02 | 5 | 0 | 5 | 5 | 20 | 70 |
|   | 50/100 | 0.005/0.01 | 0 | 0 | 0 | 0 | 0 | 45 |
|   | 50/200 | 0.005/0.02 | 0 | 0 | 0 | 0 | 20 | 55 |
| Untreated | 0 | 0 | 0 | 0 | 0 | 0 | 0 | 0 |

A is bifenthrin

B is thiamethoxam

TABLE 10

Knockdown and Mortality of Oriental Cockroach by Application of Combinations of Bifenthrin and Thiamethoxam

| Treatment | Rate of Appln. (PPM) | Rate of Appln. (% by weight) | Knockdown Rate @ 15 minute (%) | Knockdown Rate @ 30 minute (%) | Mortality Rate @ 60 minutes (%) | Mortality Rate @ 120 minutes (%) | Mortality Rate @ 4 hours (%) | Mortality Rate @ 1 day (%) |
|---|---|---|---|---|---|---|---|---|
| A | 10 | 0.001 | 0 | 0 | 0 | 0 | 0 | 0 |
|   | 50 | 0.005 | 0 | 0 | 0 | 0 | 0 | 45 |
| B | 100 | 0.01 | 0 | 0 | 0 | 0 | 0 | 20 |
|   | 200 | 0.02 | 0 | 0 | 0 | 0 | 0 | 5 |
| A + B | 10/100 | 0.001/0.01 | 0 | 0 | 0 | 0 | 0 | 5 |
|   | 10/200 | 0.001/0.02 | 0 | 0 | 0 | 0 | 0 | 40 |
|   | 50/100 | 0.005/0.01 | 0 | 0 | 0 | 0 | 0 | 35 |
|   | 50/200 | 0.005/0.02 | 0 | 0 | 0 | 0 | 10 | 65 |
| Untreated | 0 | 0 | 0 | 0 | 0 | 0 | 0 | 0 |

A is bifenthrin
B is thiamethoxam

EXAMPLE 11

Test to Determine House Fly Knockdown and Mortality Rates by Applications of Combinations of Bifenthrin and Thiamethoxam The compositions of the present invention were tested for house fly activity in the following manner:

Test compositions made up of TALSTARONE® MULTI-INSECTICIDE and a water dispersible granular of thiamethoxam (CENTRIC) in distilled water were prepared that provided appropriate rates of application of combinations of bifenthrin and thiamethoxam, as well as bifenthrin and thiamethoxam alone.

A DeVilbiss hand held sprayer was used to deliver the treatment solution at the desired volume and pressure. The house flies to be treated were collected and placed in screened 16 oz paper cups. The hand held sprayer was activated and the test compound was applied to each paper cup interior. House fly knockdown and mortality were measured. The following results were recorded:

EXAMPLE 12

Test to Determine House Fly Knockdown and Mortality Rates by Applications of Combinations of Bifenthrin and Thiamethoxam The compositions of the present invention were tested for house fly activity in the following manner:

Test compositions made up of TALSTARONE® MULTI-INSECTICIDE and a water dispersible granular of thiamethoxam (CENTRIC) in distilled water were prepared that provided appropriate rates of application of combinations of bifenthrin and thiamethoxam, as well as bifenthrin and thiamethoxam alone.

A DeVilbiss hand held sprayer was used to deliver the treatment solution at the desired volume and pressure. The house flies to be treated were collected and placed in screened 16 oz paper cups. The hand held sprayer was activated and the test compound was applied to each paper cup interior. House fly knockdown and mortality were measured. The following results were recorded:

TABLE 11

Knockdown and Mortality of House Fly by Application of Combinations of Bifenthrin and Thiamethoxam

| Treatment | Rate of Appln. (PPM) | Rate of Appln. (% by weight) | Knockdown Rate @ 15 minute (%) | Knockdown Rate @ 30 minute (%) | Knockdown Rate @ 45 minutes (%) | Knockdown Rate @ 60 minutes (%) | Knockdown Rate @ 120 minutes (%) | Knockdown Rate @ 4 hours (%) | Mortality Rate @ 1 day (%) |
|---|---|---|---|---|---|---|---|---|---|
| A | 10 | 0.001 | 0 | 0 | 6 | 19 | 19 | 48 | 3 |
|   | 50 | 0.005 | 0 | 19 | 47 | 59 | 63 | 100 | 63 |
| B | 25 | 0.0025 | 13 | 44 | 47 | 56 | 50 | 38 | 50 |
|   | 50 | 0.005 | 12 | 15 | 15 | 15 | 6 | 6 | 12 |
| A + B | 10/25 | 0.001/0.0025 | 5 | 57 | 62 | 71 | 90 | 90 | 57 |
|   | 50/25 | 0.005/0.0025 | 3 | 78 | 100 | 100 | 100 | 100 | 100 |
|   | 10/50 | 0.001/0.005 | 25 | 50 | 61 | 72 | 94 | 89 | 61 |
|   | 50/50 | 0.005/0.005 | 24 | 88 | 100 | 100 | 100 | 100 | 100 |
| Untreated | 0 | 0 | 0 | 0 | 0 | 0 | 0 | 0 | 0 |

A is bifenthrin
B is thiamethoxam

TABLE 12

Knockdown and Mortality of House Fly by Application of Combinations of Bifenthrin and Thiamethoxam

| Treatment | Rate of Appln. (PPM) | Rate of Appln. (% by weight) | Knockdown Rate @ 15 minute (%) | Knockdown Rate @ 30 minute (%) | Knockdown Rate @ 45 minutes (%) | Knockdown Rate @ 60 minutes (%) | Knockdown Rate @ 120 minutes (%) | Knockdown Rate @ 4 hours (%) | Mortality Rate @ 1 day (%) |
|---|---|---|---|---|---|---|---|---|---|
| A | 10 | 0.001 | 0 | 0 | 17 | 40 | 63 | 50 | 30 |
|   | 50 | 0.005 | 0 | 78 | 97 | 97 | 97 | 97 | 97 |
| B | 100 | 0.01 | 42 | 91 | 91 | 100 | 94 | 94 | 97 |
|   | 200 | 0.02 | 62 | 100 | 100 | 100 | 95 | 97 | 97 |
| A + B | 10/100 | 0.001/0.01 | 46 | 100 | 100 | 100 | 100 | 100 | 100 |
|   | 10/200 | 0.001/0.02 | 82 | 100 | 100 | 100 | 100 | 100 | 100 |
|   | 50/100 | 0.005/0.01 | 89 | 97 | 100 | 100 | 100 | 100 | 100 |
|   | 50/200 | 0.005/0.02 | 97 | 100 | 100 | 100 | 100 | 100 | 100 |
| Untreated | 0 | 0 | 0 | 0 | 0 | 0 | 0 | 0 | 0 |

A is bifenthrin
B is thiamethoxam

EXAMPLE 13

Test to Determine German Cockroach Mortality Rates by Applications of Combinations of Bifenthrin and Clothianidin The compositions of the present invention were tested for German cockroach activity in the following manner:

Test compositions made up of TALSTARONE® MULTI-INSECTICIDE and a 16% a.i. water dispersible granular of clothianidin in distilled water were prepared that provided appropriate rates of application of combinations of bifenthrin and clothianidin, as well as bifenthrin and clothianidin alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male German cockroaches were placed inside each PVC ring. The sprayer was activated and the test compound was applied to each PVC ring interior. German cockroach mortality was measured. The following results were recorded:

TABLE 13

Mortality of German Cockroach by Application of Combinations of Bifenthrin and Clothianidin

| Treatment | Rate of Appln. (PPM) | Rate of Appln. (% by weight) | Mortality Rate @ 60 minutes (%) | Mortality Rate @ 120 minutes (%) | Mortality Rate @ 1 day (%) | Mortality Rate @ 2 days (%) | Mortality Rate @ 4 days (%) |
|---|---|---|---|---|---|---|---|
| A | 10 | 0.001 | 8 | 33 | 35 | 60 | 100 |
|   | 50 | 0.005 | 15 | 48 | 58 | 100 | 100 |
| B | 100 | 0.01 | 18 | 35 | 58 | 75 | 85 |
|   | 200 | 0.02 | 38 | 60 | 73 | 98 | 100 |
| A + B | 10/100 | 0.001/0.01 | 35 | 55 | 98 | 98 | 100 |
|   | 10/200 | 0.001/0.02 | 60 | 83 | 100 | 100 | 100 |
|   | 50/100 | 0.005/0.01 | 45 | 63 | 100 | 100 | 100 |
|   | 50/200 | 0.005/0.02 | 65 | 75 | 100 | 100 | 100 |
| Untreated | 0 | 0 | 0 | 0 | 0 | 3 | 5 |

A is bifenthrin
B is clothianidin

EXAMPLE 14

Test to Determine American Cockroach Knockdown and Mortality Rates by Applications of Combinations of Bifenthrin and Clothianidin The compositions of the present invention were tested for American cockroach activity in the following manner:

Test compositions made up of TALSTARONE® MULTI-INSECTICIDE and a 16% a.i. water dispersible granular of clothianidin in distilled water were prepared that provided appropriate rates of application of combinations of bifenthrin and clothianidin, as well as bifenthrin and clothianidin alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male American cockroaches were placed inside each PVC ring. The sprayer was activated and the test compound was applied to each PVC ring interior. American cockroach knockdown and mortality were measured. The following results were recorded:

EXAMPLE 15

Test to Determine Oriental Cockroach Knockdown and Mortality Rates by Applications of Combinations of Bifenthrin and Clothianidin The compositions of the present invention were tested for Oriental cockroach activity in the following manner:

Test compositions made up of TALSTARONE® MULTI-INSECTICIDE and a 16% a.i. water dispersible granular of clothianidin in distilled water were prepared that provided appropriate rates of application of combinations of bifenthrin and clothianidin, as well as bifenthrin and clothianidin alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. A desired number of 4.0" sieve circles were marked on the aluminum foil with a permanent marker. The inside of a desired number of PVC rings were coated with a petroleum jelly/mineral oil mixture (1:2 ratio). The PVC rings were place on the sieve circles. 10 male Oriental cockroaches were placed inside each PVC ring. The sprayer was activated and the test compound was applied to each PVC ring interior. Oriental cockroach knockdown and mortality were measured. The following results were recorded:

TABLE 14

Knockdown and Mortality of American Cockroach by Application of Combinations of Bifenthrin and Clothianidin

| Treatment | Rate of Appln. (PPM) | Rate of Appln. (% by weight) | Knockdown Rate @ 10 minute (%) | Knockdown Rate @ 15 minute (%) | Knockdown Rate @ 30 minute (%) | Mortality Rate @ 60 minute (%) | Mortality Rate @ 120 minutes (%) | Mortality Rate @ 4 hours (%) | Mortality Rate @ 1 day (%) | Mortality Rate @ 2 days (%) |
|---|---|---|---|---|---|---|---|---|---|---|
| A | 10 | 0.001 | 0 | 0 | 0 | 0 | 0 | 0 | 10 | 30 |
|   | 50 | 0.005 | 5 | 10 | 5 | 0 | 0 | 35 | 40 | 55 |
| B | 100 | 0.01 | 0 | 10 | 25 | 0 | 0 | 35 | 50 | 60 |
|   | 200 | 0.02 | 0 | 0 | 0 | 0 | 5 | 20 | 60 | 60 |
| A + B | 10/100 | 0.001/0.01 | 5 | 5 | 10 | 0 | 5 | 25 | 35 | 35 |
|   | 10/200 | 0.001/0.02 | 0 | 0 | 0 | 0 | 10 | 25 | 85 | 85 |
|   | 50/100 | 0.005/0.01 | 5 | 0 | 20 | 0 | 0 | 35 | 50 | 50 |
|   | 50/200 | 0.005/0.02 | 0 | 5 | 15 | 0 | 10 | 70 | 90 | 90 |
| Untreated | 0 | 0 | 0 | 0 | 0 | 0 | 0 | 0 | 0 | 0 |

A is bifenthrin

B is clothianidin

TABLE 15

Knockdown and Mortality of Oriental Cockroach by Application of Combinations of Bifenthrin and Clothianidin

| Treatment | Rate of Appln. (PPM) | Rate of Appln. (% by weight) | Knockdown Rate @ 10 minute (%) | Knockdown Rate @ 15 minute (%) | Knockdown Rate @ 30 minute (%) | Mortality Rate @ 60 minute (%) | Mortality Rate @ 120 minute (%) | Mortality Rate @ 4 hours (%) | Mortality Rate @ 1 day (%) | Mortality Rate @ 2 days (%) |
|---|---|---|---|---|---|---|---|---|---|---|
| A | 10 | 0.001 | 0 | 0 | 0 | 0 | 0 | 0 | 0 | 3 |
|   | 50 | 0.005 | 0 | 0 | 0 | 0 | 0 | 10 | 20 | 23 |
| B | 100 | 0.01 | 0 | 0 | 0 | 0 | 5 | 8 | 50 | 50 |
|   | 200 | 0.02 | 0 | 0 | 3 | 3 | 3 | 15 | 50 | 50 |
| A + B | 10/100 | 0.001/0.01 | 5 | 0 | 0 | 0 | 0 | 13 | 43 | 45 |
|   | 10/200 | 0.001/0.02 | 0 | 0 | 0 | 0 | 0 | 18 | 48 | 48 |
| A + B | 50/100 | 0.005/0.01 | 0 | 5 | 5 | 8 | 13 | 50 | 50 | 50 |
|   | 50/200 | 0.005/0.02 | 0 | 0 | 0 | 0 | 18 | 48 | 50 | 50 |
| Untreated | 0 | 0 | 0 | 0 | 0 | 0 | 0 | 0 | 0 | 0 |

A is bifenthrin
B is clothianidin

EXAMPLE 16

Test to Determine Red Imported Fire Ant Knockdown and Mortality Rates by Applications of Combinations of Bifenthrin and Clothianidin The compositions of the present invention were tested for red imported fire ant activity in the following manner:

Test compositions made up of TALSTARONE® MULTI-INSECTICIDE and a 16% a.i. water dispersible granular of clothianidin in distilled water were prepared that provided appropriate rates of application of combinations of bifenthrin and clothianidin, as well as bifenthrin and clothianidin alone.

The spray chamber was then calibrated to deliver the treatment solution at the desired volume and pressure over the desired area on the chamber shelf. Spray chamber shelf height was adjusted to approximately 18 inches from the spray tip. The shelf was then covered with aluminum foil and the center of the shelf from front-to-back and end-to-end was determined. The red imported fire ants to be treated were collected and placed in screened 16 oz paper cups. The paper cups were placed onto the aluminum foil on the spray chamber shelf. The sprayer was activated and the test compound was applied to each paper cup interior. Red imported fire ant knockdown and mortality were measured. The following results were recorded:

TABLE 16

Knockdown and Mortality of Red Imported Fire Ant by Application of Combinations of Bifenthrin and Clothianidin

| Treatment | Rate of Appln. (PPM) | Rate of Appln. (% by weight) | Knockdown Rate @ 5 minute (%) | Knockdown Rate @ 10 minute (%) | Knockdown Rate @ 15 minute (%) | Knockdown Rate @ 30 minutes (%) | Mortality Rate @ 60 minutes (%) | Mortality Rate @ 120 minutes (%) | Mortality Rate @ 4 hours (%) |
|---|---|---|---|---|---|---|---|---|---|
| A | 10 | 0.001 | 30 | 93 | 95 | 100 | 65 | 100 | 100 |
|   | 50 | 0.005 | 10 | 70 | 95 | 100 | 100 | 100 | 100 |
| B | 100 | 0.01 | 35 | 70 | 78 | 100 | 75 | 83 | 98 |
|   | 200 | 0.02 | 20 | 30 | 53 | 65 | 53 | 88 | 100 |
| A + B | 10/100 | 0.001/0.01 | 8 | 78 | 100 | 100 | 100 | 100 | 100 |
|   | 10/200 | 0.001/0.02 | 15 | 60 | 95 | 100 | 100 | 100 | 100 |
|   | 50/100 | 0.005/0.01 | 25 | 90 | 100 | 100 | 100 | 100 | 100 |
|   | 50/200 | 0.005/0.02 | 15 | 88 | 100 | 100 | 100 | 100 | 100 |
| Untreated | 0 | 0 | 0 | 0 | 0 | 0 | 0 | 0 | 0 |

A is bifenthrin
B is clothianidin

EXAMPLE 17

Test to Determine House Fly Knockdown and Mortality Rates by Applications of Combinations of Bifenthrin and Clothianidin The compositions of the present invention were tested for house fly activity in the following manner:

Test compositions made up of TALSTARONE® MULTI-INSECTICIDE and a 16% a.i. water dispersible granular of clothianidin in distilled water were prepared that provided appropriate rates of application of combinations of bifenthrin and clothianidin, as well as bifenthrin and clothianidin alone.

A DeVilbiss hand held sprayer was used to deliver the treatment solution at the desired volume and pressure. The house flies to be treated were collected and placed in screened 16 oz paper cups. The hand held sprayer was activated and the test compound was applied to each paper cup interior. House fly knockdown and mortality were measured. The following results were recorded:

TABLE 17

Knockdown and Mortality of House Flies by Application of Combinations of Bifenthrin and Clothianidin

| Treatment | Rate of Appln. (PPM) | Rate of Appln. (% by weight) | Knockdown Rate @ 15 minute (%) | Knockdown Rate @ 30 minute (%) | Knockdown Rate @ 45 minutes (%) | Knockdown Rate @ 60 minutes (%) | Knockdown Rate @ 120 minutes (%) | Knockdown Rate @ 180 minutes (%) | Knockdown Rate @ 4 hours (%) | Mortality Rate @ 1 day (%) |
|---|---|---|---|---|---|---|---|---|---|---|
| A | 10 | 0.001 | 0 | 0 | 0 | 0 | 3 | 3 | 3 | 3 |
|  | 50 | 0.005 | 3 | 55 | 66 | 68 | 74 | 74 | 76 | 79 |
| B | 100 | 0.01 | 97 | 100 | 100 | 100 | 47 | 59 | 44 | 88 |
|  | 200 | 0.02 | 94 | 100 | 100 | 100 | 71 | 38 | 47 | 97 |
| A + B | 10/100 | 0.001/0.01 | 65 | 97 | 100 | 100 | 100 | 100 | 84 | 100 |
|  | 10/200 | 0.001/0.02 | 93 | 100 | 100 | 100 | 100 | 100 | 100 | 100 |
|  | 50/100 | 0.005/0.01 | 91 | 94 | 100 | 100 | 97 | 91 | 85 | 97 |
|  | 50/200 | 0.005/0.02 | 100 | 100 | 100 | 100 | 100 | 100 | 100 | 100 |
| Untreated | 0 | 0 | 0 | 0 | 0 | 0 | 0 | 0 | 0 | 0 |

A is bifenthrin
B is clothianidin

EXAMPLE 18

Test to Determine Yellow Fever Mosquito Knockdown and Mortality Rates by Applications of Combinations of Bifenthrin and Clothianidin The compositions of the present invention were tested for Yellow Fever Mosquito activity in the following manner:

Test compositions made up of TALSTARONE® MULTI-INSECTICIDE and a 16% a.i. water dispersible granular of clothianidin in distilled water were prepared that provided appropriate rates of application of combinations of bifenthrin and clothianidin, as well as bifenthrin and clothianidin alone.

A DeVilbiss hand held sprayer was used to deliver the treatment solution at the desired volume and pressure. The Yellow Fever Mosquitoes to be treated were collected and placed in screened 16 oz paper cups. The hand held sprayer was activated and the test compound was applied to each paper cup interior. Yellow Fever Mosquito knockdown and mortality were measured. The following results were recorded:

TABLE 18

Knockdown and Mortality of Yellow Fever Mosquito by Application of Combinations of Bifenthrin and Clothianidin

| Treatment | Rate of Appln. (PPM) | Rate of Appln. (% by weight) | Knockdown Rate @ 15 minute (%) | Knockdown Rate @ 30 minute (%) | Mortality Rate @ 45 minutes (%) | Mortality Rate @ 60 minutes (%) | Mortality Rate @ 120 minutes (%) | Mortality Rate @ 180 minute (%) | Mortality Rate @ 4 hours (%) | Mortality Rate @ 1 day (%) |
|---|---|---|---|---|---|---|---|---|---|---|
| A | 10 | 0.001 | 27 | 97 | 100 | 100 | 100 | 100 | 100 | 100 |
|  | 50 | 0.005 | 90 | 100 | 100 | 100 | 100 | 100 | 100 | 100 |

TABLE 18-continued

Knockdown and Mortality of Yellow Fever Mosquito by Application of Combinations of Bifenthrin and Clothianidin

| Treatment | Rate of Appln. (PPM) | Rate of Appln. (% by weight) | Knockdown Rate @ 15 minute (%) | Knockdown Rate @ 30 minute (%) | Mortality Rate @ 45 minutes (%) | Mortality Rate @ 60 minutes (%) | Mortality Rate @ 120 minutes (%) | Mortality Rate @ 180 minute (%) | Mortality Rate @ 4 hours (%) | Mortality Rate @ 1 day (%) |
|---|---|---|---|---|---|---|---|---|---|---|
| B | 100 | 0.01 | 0 | 0 | 7 | 7 | 3 | 7 | 10 | 53 |
|  | 200 | 0.02 | 3 | 11 | 17 | 31 | 37 | 40 | 40 | 60 |
| A + B | 10/100 | 0.001/0.01 | 17 | 100 | 100 | 100 | 100 | 100 | 100 | 100 |
|  | 10/200 | 0.001/0.02 | 39 | 94 | 100 | 100 | 100 | 100 | 100 | 100 |
|  | 50/100 | 0.005/0.01 | 97 | 100 | 100 | 100 | 100 | 100 | 100 | 100 |
|  | 50/200 | 0.005/0.02 | 100 | 100 | 100 | 100 | 100 | 100 | 100 | 100 |
| Untreated | 0 | 0 | 0 | 0 | 0 | 0 | 0 | 0 | 0 | 0 |

A is bifenthrin
B is clothianidin

In the context of the present invention, the term "insecticide" refers to the active chemical compound or ingredient, such as bifenthrin, cypermethrin, zeta cypermethrin, lambda-cyhalothrin, betacyhalothrin, alphacypermethrin, tralomethrin, deltamethrin, cyfluthrin, beta-cyfluthrin, esfenvalerate, fluvalinate, etofenprox, permethrin, metofluthrin, resmethrin, bioresmethrin, allethrin, bioallethrin, s-bioallethrin, tetramethrin, imidacloprid, nithiazine, thiamethoxam, dinotefuran, nitenpyram, thiacloprid, clothianidin, or chlorfenapyr, that kills or causes knockdown of insects. The term "bifenthrin" means 2-methylbiphenyl-3-ylmethyl (Z)-(1RS)-cis-3-(2-chloro-3,3,3-trifluoroprop-1-enyl)-2,2-dimethylcyclopropanecarboxylate or 2-methylbiphenyl-3-ylmethyl (Z)-(1RS,3RS)-3-(2-chloro-3,3,3-trifluoroprop-1-enyl)-2,2-dimethylcyclopropanecarboxylate, CAS Registry Number 82657-04-3. The term "imidacloprid" means (EZ)-1-(6-chloro-3-pyridylmethyl)-N-nitroimidazolidin-2-ylideneamine, CAS Registry Number 138261-41-3. The term "thiamethoxam" means (EZ)-3-(2-chloro-1,3-thiazol-5-ylmethyl)-5-methyl-1,3,5-oxadiazinan-4-ylidene(nitro)amine, CAS Registry Number 153719-23-4. The term "clothianidin" means (E)-1-(2-chloro-1,3-thiazol-5-ylmethyl)-3-methyl-2-nitroguanidine, CAS Registry Number 210880-92-5 (formerly 205510-53-8). The term "liquid insecticide" refers to a formulation of an insecticide where the formulation can be dispensed in an aqueous medium prior to its application to a locus where insect control is desired. The term "locus" refers to any location where control of insects is needed or expected to be needed. The term "general household pest" refers to any insect or pest, such as German cockroach, American cockroach, Smokey-Brown cockroach, Oriental cockroach, house fly, biting fly, filth fly, red imported fire ant (RIFA), odorous house ant, carpenter ant, pharaoh ant, Argentine ant, mosquito, tick, flea, sowbug, pillbug, centipede, spider, silverfish, scorpion and bed bug, that cause harm or nuisance to person or property. The term "knockdown" refers to the quick, short-term immobilization or death of the insects. The term "mortality" refers to the death of the insects. The term "% by weight" refers to the weight of the insecticide or specified component as a percent of the total weight of the composition (e.g. including the aqueous medium, other insecticides, surfactants, wetting agents, freeze/thaw agents and combinations thereof).

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for controlling general household pests comprising applying an insecticidally effective amount of a composition wherein the insecticide consists of a mixture of
   i) from 0.001% by weight to 0.06% by weight bifenthrin and
   ii) from 0.001% by weight to 0.20% by weight of a second insecticide selected from the group consisting of imidacloprid, thiamethoxam, and clothianidin;
to a locus where general household pest control is needed or expected to be needed, wherein said locus is selected from a general household pest-infested structure, a structure that is expected to be general household pest-infested, or a location adjacent to said structures and said general household pest is selected from German cockroach, American cockroach, Smokey-Brown cockroach, Oriental cockroach, house fly, biting fly, filth fly, red imported fire ant (RIFA), odorous house ant, carpenter ant, pharaoh ant, Argentine ant, mosquito, tick, flea, sowbug, pillbug, centipede, spider, silverfish, scorpion and bed bug.

2. The method of claim 1, wherein said general household pest is selected from German cockroach, American cockroach, Oriental cockroach, house fly, \red imported fire ant (RIFA), and mosquito.

3. The method of claim 1, wherein the second insecticide is imidacloprid.

4. The method of claim 3, wherein the mixture contains from 0.01% to 0.10% by weight of the imidacloprid.

5. The method of claim 1, wherein the second insecticide is thiamethoxam.

6. The method of claim 5, wherein the mixture contains from 0.0025% to 0.0225% by weight of the thiamethoxam.

7. The method of claim 1, wherein the second insecticide is clothianidin.

8. The method of claim 7, wherein the mixture contains from 0.01% to 0.02% by weight of the clothianidin.

* * * * *